US008163977B2

(12) United States Patent
Chakraborty et al.

(10) Patent No.: US 8,163,977 B2
(45) Date of Patent: Apr. 24, 2012

(54) EXTRA-CELLULAR MATRIX LOCALIZED FERRITIN FOR IRON UPTAKE, STORAGE, AND STRESS TOLERANCE

(76) Inventors: Niranjan Chakraborty, New Delhi (IN); Subhra Chakraborty, New Delhi (IN); Asis Datta, New Delhi (IN); Deepti Bhusan, New Delhi (IN)

( * ) Notice: Subject to any disclaimer, the term of this patent is extended or adjusted under 35 U.S.C. 154(b) by 386 days.

(21) Appl. No.: 12/308,141

(22) PCT Filed: Jun. 8, 2007

(86) PCT No.: PCT/IN2007/000231
§ 371 (c)(1),
(2), (4) Date: Oct. 19, 2009

(87) PCT Pub. No.: WO2007/141808
PCT Pub. Date: Dec. 13, 2007

(65) Prior Publication Data
US 2010/0251426 A1    Sep. 30, 2010

(30) Foreign Application Priority Data

Jun. 8, 2006    (IN) .............................. 137/DEL/2006

(51) Int. Cl.
*A01H 5/00* (2006.01)
*A01H 5/10* (2006.01)
*C12N 15/85* (2006.01)

(52) U.S. Cl. .......................... 800/278; 435/468; 435/419
(58) Field of Classification Search ........................ None
See application file for complete search history.

(56) References Cited

U.S. PATENT DOCUMENTS
2005/0108791 A1* 5/2005 Edgerton ...................... 800/284

FOREIGN PATENT DOCUMENTS
WO    WO98/46775    * 10/1998
WO    WO-98/46775 A1    10/1998

OTHER PUBLICATIONS

Masuda et al (Journal of Biological Chemistry, 2010 vol. 285, No. 6, p. 4049-4059).*
"International Application Serial No. PCT/IN2007/000231, International Search Report mailed Apr. 10, 2008", 4 pgs.
"Vigna unguiculata ferritin subunit cowpea2 precursor, mRNA, nuclear gene encoding chloroplast protein, complete cds.", *Database EMBL [online]. EBI* Accession No. EMBL: AFO52058, (1998), 2 pgs.
Ambe, S., et al., "Mössbauer Study of Iron in Soybean Seeds", *Journal of Agricultural and Food Chemistry*, 35(3), (1987), 292-296.
Ames, B., "Assay of Inorganic Phosphate, Total Phosphate and Phosphatases", *Methods in Enzymology*, vol. VIII—*Complex Carbohydrates*, (Neufeld, E. F., Editors, et al, Academic Press, Inc.), (1966), 115-118.
Averyhart-Fullard, V., et al., "A hydroxyproline-rich protein in the soybean cell wall", *Proc. Natl. Acad. Sci. USA*, 85, (1988), 1082-1085.
Beard, J. L., et al., "Iron Status and Neural Functioning", *Annual Reviews in Nutrition*, 23, (2003), 41-58.

Bhushan, D., et al., "Extracellular Matrix Proteome of Chickpea (*Cicer arietinum* L.) Illustrates Pathway Abundance, Novel Protein Functions and Evolutionary Perspect", *Journal of Proteome Research*, 5(7), (2006), 1711-1720.
Briat, J.-F., et al., "Regulation of plant ferritin synthesis: how and why", *CMLS Cellular and Molecular Life Sciences*, 56, (1999), 155-166.
Casanueva, E., et al., "Iron and Oxidative Stress in Pregnancy", *Journal of Nutrition*, 133(5), (2003), 1700S-1708S.
Deåk, M., et al., "Plants ectopically expressing the iron-binding protein, ferritin, are tolerant to oxidative damage and pathogens", *Nature Biotechnology*, 17(2), (1999), 192-196.
Dreger, M., "Proteome analysis at the level of subcellular structures", *Eur. J. Biochem.*, 270, (2003), 589-599.
Ferreira, C., et al., "Early Embryonic Lethality of H Ferritin Gene Deletion in Mice", *The Journal of Biological Chemistry*, 275(5), (2000), 3021-3024.
Fobis-Loisy, I., et al., "Structure and Differential Expression of Tow Maize Ferritin Genes in Response to Iron and Abscisic Acid", *European Journal of Biochemistry*, 231(3), (1995),609-619.
Harrison, P. M., et al., "The ferritins: molecular properties, iron storage function and cellular regulation", *Biochimica et Biophysica Acta*, 1275, (1996),161-203.
Horsch, R. B., et al., "A Simple and General Method for Transferring Genes into Plants", *Science*, 227(4691), (Mar. 8, 1985),1229-1231.
Hurkman, W. J., et al., "Solubilization of Plant Membrane Proteins for Analysis by Two-Dimensional Gel Electrophoresis", *Plant Physiol.*, 81, (1986), 802-806.
Jiang, T.-B., "Isolation and Expression Pattern Analysis of Two Ferritin Genes in Tobacco", *Journal of Integrative Plant Biology*, 47(4), (2005), 477-486.
Kwok, J. C., et al., "Examination of the Mechanism(s) Involved in Doxorubicin-Mediated Iron Accumulation in Ferritin: Studies Using Metabolic Inhibitors, Protein Synthesis Inhibitors, and Lysosomotropic Agents", *Molecular Pharmacology*, 65(1), (2004), 181-195.
Larsson, C., et al., "Isolation of Highly Purified Plant Plasma Membranes and Separation of Inside-Out and Right-Side-Out Vesicles", *Methods in Enzymology*, vol. 228—*Aqueous Two-Phase Systems*, (Walter, H., et al., Editors, Academic Press, Inc.),(1994), 451-469.
Petit, J.-M., et al., "Structure and differential expression of the four members of the *Arabidopsis thaliana* ferritin gene family", *Biochemical Journal*, 359(3), (2001), 575-582.
Shinozaki, K., et al., "Gene Expression and Signal Transduction in Water-Stress Response", *Plant Physiol.*, 115, (1997), 327-334.
Shinozaki, K., et al., "Molecular responses to dehydration and low temperature: differences and cross-talk between two stress signalling pathways", *Current Opinion in Plant Biology*, 3, (2000), 217-223.

(Continued)

*Primary Examiner* — Anne Kubelik
*Assistant Examiner* — Lee Visone
(74) *Attorney, Agent, or Firm* — Schwegman, Lundberg & Woessner, P.A.

(57) ABSTRACT

The present invention relates to environmental stress responsive protein ferritin (CaFer1) of chickpea. The invention discloses identification, isolation and cloning of ECM-localized ferritin (CaFer1) of chickpea and its multifunctional role in nutrient uptake, storage and stress tolerance. Comparative proteomic analysis of the chickpea extra-cellular (ECM) was performed to identify novel components of dehydration stress signaling. In addition, the present invention relates a method for producing environmental stress tolerant transgenic plants over-expressing the said CaFer1 gene. The present invention further provides dehydration stress tolerant transgenic plants overexpressing dehydration-responsive extra cellular matrix (ECM) protein ferritin (CaFer1).

18 Claims, 6 Drawing Sheets

OTHER PUBLICATIONS

Strozycki, P. M., et al., "Differential expression and evolutionary analysis of the three ferritin genes in the legume plant *Lupinas luteus*", *Physiologia Plantarum*, 118(3), (2003), 380-389.

Stuart, D. A., et al., "Purification and Characterization of a Salt-extractable Hydroxyproline-rich Glycoprotein from Aerated Carrot Discs", *Plant Physiol.*, 66(5), (1980), 787-792.

Van Haute, E., et al., "Intergeneric transfer and exchange recombination of restriction fragments cloned in pBR322: a novel strategy for the reversed genetics of the Ti plasmids of *Agrobacterium tumefaciens*", *The EMBO Journal*, 2(3), (1983), 411-417.

Wardrop, A. J., et al., "Occurrence and expression of members of the ferritin gene family in cowpeas", *Biochemical Journal*, 337(3), (1999),523-530.

Zhou, Z. Q., et al., "The cloning of apple ferritin gene (Apfl) from Malus xiaojinensis Cheng et Jiang and its structure analysis", *Chinese Journal of Biotechnology*, 17(3), (Abstract Only), PMID: 11517616 [PubMed—indexed for MEDLINE],(2001), 1 pg.

* cited by examiner

SEQUENCE LISTING

<160> NUMBER OF SEQ ID NOS: 6

<210> SEQ ID NO 1
<211> LENGTH: 19
<212> TYPE: DNA
<213> ORGANISM: Artificial
<220> FEATURE:
<223> OTHER INFORMATION: Synthetic oligonucleotide

<400> SEQUENCE: 1
gaagaaagag agcatgctg                                                19

<210> SEQ ID NO 2

<211> LENGTH: 458
<212> TYPE: DNA
<213> ORGANISM: Artificial
<220> FEATURE:
<223> OTHER INFORMATION: Synthetic oligonucleotide

<400> SEQUENCE: 2

```
gaagaagaaa gagagcatgc tgagaaattg atggaatatc agaacaaaag gggtggaaaa      60
gtgaagttgc aatctatagt gaagccgctt tctgagtttg atcatgctga taagggtgat     120
gcgctttacg caatggaact cgcactgtca ttggagaagc taaccaatga aaagctcctt     180
aacctgcaca atgttgcctc gaagaatggt gacgtgcaat tgacagactt tgtggaaagt     240
gagttttttgg gtgaacaggt ggaagccatc aaaaaaatct cagagtttgt cgctcagctt    300
agaagagttg gcaaaggaca cggtgtctgg cactttgatc agatgttgct caacgaggaa     360
gcagctgcag cttgatgatt acattttttgt ctccgttttc agtcattgta tctgtttctg    420
ctagaactac aagttgacac tgaaatcgtc agctgaat                              458
```

<210> SEQ ID NO 3
<211> LENGTH: 1078
<212> TYPE: DNA
<213> ORGANISM: Artificial
<220> FEATURE:
<223> OTHER INFORMATION: Synthetic oligonucleotide

<400> SEQUENCE: 3

```
acgggatcgg ccattacggc cggggtcaca cacattcatc aaaacccttt ctattccatt      60
ttcctccgat tttctttctt tccgttttcg ttccgtcgaa aattccctaa ccatgcttct     120
cagagccgct gtaaccgctt cttcttcttc ctcacttcct ctcttcaatt ctgaaaactc     180
gcgtttggct ccgattcttc acagaggagg taaattggac cgattggttt tttccgccac     240
caaaggctct agcaataacc gtattctaac cggtgttttg tttgaaccgt ttgaagaggt     300
taaaaaggaa ctcgatcttg ttcccattgt tcctcaagat tccttagctc gtcgtaagtt     360
tcatgatgca tctgaagctg ctatcaatga acaaatcaat gtggagtata atgtatccta     420
cgtttatcat gcaatgtatg cgtacttcga tagggataat gttgccctaa ggggtcttgc     480
taaatttttt aaggaatcta gtgaagagga aagggagcat gctgagaaat tgatggaata     540
tcagaacaaa aggggtggaa aagtgaagtt gcaatctata gtgaagccgc tttctgagtt     600
tgatcatgct gataagggtg atgcgcttta cgcaatggaa ctcgcactgt cattggagaa     660
gctaaccaat gaaaagctcc ttaacctgca caatgttgcc tcgaagaatg gtgacgtgca     720
attgacagac tttgtggaaa gtgagttttt gggtgaacag gtggaagcca tcaaaaaaat     780
ctcagagttt gtcgctcagc ttagaagagt tggcaaagga cacggtgtct ggcactttga     840
tcagatgttg ctcaacgagg aagcagctgc agcttgatga ttacattttt gtctccgttt     900
tcagtcattg tatctgtttt gctagaacta agttgaca ctgaatcgta gctgaataaa      960
attaatgtgg aatgttttgg gtcattgtta attttcagtt tatttacctc tttctcccca    1020
aaaaaaaaaa aaaaaaaaaa aaaaaacatg tcggccgcct cggcccagtc gactctag     1078
```

<210> SEQ ID NO 4
<211> LENGTH: 254
<212> TYPE: PRT
<213> ORGANISM: Artificial
<220> FEATURE:
<223> OTHER INFORMATION: Synthetic oligonucleotide

<400> SEQUENCE: 4

```
Met Leu Leu Arg Ala Ala Val Thr Ala Ser Ser Ser Ser Leu Pro
1               5                   10                  15

Leu Phe Asn Ser Glu Asn Ser Arg Leu Ala Pro Ile Leu His Arg Gly
            20                  25                  30

Gly Lys Leu Asp Arg Leu Val Phe Ser Ala Thr Lys Gly Ser Ser Asn
        35                  40                  45

Asn Arg Ile Leu Thr Gly Val Leu Phe Glu Pro Phe Glu Glu Val Lys
    50                  55                  60

Lys Glu Leu Asp Leu Val Pro Ile Val Pro Gln Asp Ser Leu Ala Arg
65                  70                  75                  80

Arg Lys Phe His Asp Ala Ser Glu Ala Ala Ile Asn Glu Gln Ile Asn
                85                  90                  95

Val Glu Tyr Asn Val Ser Tyr Val Tyr His Ala Met Tyr Ala Tyr Phe
            100                 105                 110

Asp Arg Asp Asn Val Ala Leu Arg Gly Leu Ala Lys Phe Phe Lys Glu
            115                 120                 125

Ser Ser Glu Glu Glu Arg Glu His Ala Glu Lys Leu Met Glu Tyr Gln
    130                 135                 140

Asn Lys Arg Gly Gly Lys Val Lys Leu Gln Ser Ile Val Lys Pro Leu
145                 150                 155                 160

Ser Glu Phe Asp His Ala Asp Lys Gly Asp Ala Leu Tyr Ala Met Glu
                165                 170                 175

Leu Ala Leu Ser Leu Glu Lys Leu Thr Asn Glu Lys Leu Leu Asn Leu
            180                 185                 190

His Asn Val Ala Ser Lys Asn Gly Asp Val Gln Leu Thr Asp Phe Val
            195                 200                 205

Glu Ser Glu Phe Leu Gly Glu Gln Val Glu Ala Ile Lys Lys Ile Ser
210                 215                 220

Glu Phe Val Ala Gln Leu Arg Arg Val Gly Lys Gly His Gly Val Trp
225                 230                 235                 240

His Phe Asp Gln Met Leu Leu Asn Glu Glu Ala Ala Ala Ala
                245                 250
```

<210> SEQ ID NO 5
<211> LENGTH: 56
<212> TYPE: DNA
<213> ORGANISM: Artificial
<220> FEATURE:
<223> OTHER INFORMATION: Synthetic oligonucleotide

<400> SEQUENCE: 5
ggggacaagt tgtacaaaa aagcaggctc aacccacgct tgtatgcat atttcg    56

<210> SEQ ID NO 6
<211> LENGTH: 53
<212> TYPE: DNA
<213> ORGANISM: Artificial
<220> FEATURE:
<223> OTHER INFORMATION: Synthetic oligonucleotide

<400> SEQUENCE: 6
ggggaccact tgtacaaga aagctgggtc tccccaatga aagagccaac tcc    53

EXTRA-CELLULAR MATRIX LOCALIZED FERRITIN FOR IRON UPTAKE, STORAGE, AND STRESS TOLERANCE

RELATED APPLICATIONS

This application is a national stage application under 35 U.S.C. 371 of PCT/IN2007/000231, filed Jun. 8, 2007, and published as WO 2007/141808 A2, on Dec. 13, 2007, and republished as Wo2007/141808 A3, on Dec. 13, 2007, which claims priority under 35 U.S.C. 119 to Indian Application No. 1371/DEL/2006, filed Jun. 8, 2006, which applications and publication are incorporated herein by reference and made a part hereof in their entirety.

FIELD OF INVENTION

The present invention relates to environmental stress responsive protein ferritin (CaFer1) from chickpea. The invention further relates to the ECM-localized ferritin protein CaFer1, identification, isolation and cloning of the gene encoding same from chickpea and its multifunctional role in nutrient uptake, storage and stress tolerance.

BACKGROUND OF THE INVENTION

Plants are adequately protected by the presence of multiple protein components in different organelles such as chloroplast, cytoplasm, mitochondria and peroxisomes. Therefore, investigation of organellar-specific proteome is important to understand the mechanism of function of protein subset in which they exert their particular function (Dreger, 2003).

In plants, cell wall or extra-cellular matrix (ECM) serves as the repository for most of the components of cell signaling process. In legumes, the majority of iron is represented by ferritin (Ambe et al., 1987; Burton et al., 1998) and used for nitrogen fixation by, nodules. Accumulation of nodule ferritin is developmentally regulated. Iron is recovered by nodule ferritin during nodule senescence and recycled by a mechanism yet to be identified. Classically, iron storage protein, ferritin, is reported to be present in the plastids. However, there are reports of ferritins being localized to other cellular compartments such as mitochondria and nucleus (Harrison and Arosio, 1996; Kwok and Richardson, 2004).

With completion of genome sequencing exercises and development of analytical methods for protein characterization, proteomics has become a major tool of functional genomics. This technology allows the global analyses of gene products in cells, organelles, and physiological state of cells. However, the application of proteomic approach at whole cell level is limited by several factors such as protein abundance, size, hydrophobicity, and other electrophoretic properties. The compartment specific proteome is thus important because fractionated subsets of proteins provide the suitable information in which they exert their particular function.

SUMMARY

The present invention relates to environmental stress responsive protein ferritin (SEQ ID NO: 4) (CaFer1) of chickpea. The invention further relates to identification, isolation and cloning of ECM-localized ferritin (CaFer1) of chickpea (SEQ ID NO: 3) and its multifunctional role in nutrient uptake, storage and stress tolerance.

One aspect of the present invention relates to an isolated polypeptide having environmental stress responsive activity comprising the amino acid sequence as set forth in the SEQ ID NO: 4.

Another aspect of the present invention relates to a nucleotide sequence having at least 90% identity with the nucleotide sequence as set forth in SEQ ID NO: 3, wherein said nucleotide sequence encodes for the polypeptide having the amino acid sequence as set forth in the SEQ ID NO: 4.

Yet another aspect of the present invention relates to an isolated nucleic acid having at least 300 contiguous nucleotide sequence as set forth in SEQ ID NO: 3, wherein said nucleotide sequence encodes a polypeptide comprising the amino acid sequence as set forth in the SEQ ID NO: 4.

Still yet another aspect of the present invention relates to a recombinant vector comprising the nucleic acid having nucleotide sequence as set forth in SEQ ID NO: 3.

Further the present invention provides a method for producing a transformed plant cell, plant or plant part expressing environmental stress responsive protein ferritin 1, said method comprising transforming a plant cell, plant or plant part with a nucleotide sequence having at least 90% identity with the nucleotide sequence as set forth in SEQ ID NO: 3, wherein said nucleotide sequence encodes ferritin protein comprising amino acid sequence as set forth in the SEQ ID NO: 4.

The present invention also provides a method for producing a transformed plant cell, plant or plant part expressing environmental stress responsive protein ferritin 1, said method comprising transforming a plant cell, plant or plant part with a nucleotide sequence having the nucleotide sequence as set forth in SEQ ID NO: 3, wherein said nucleotide sequence encodes ferritin protein comprising amino acid sequence as set forth in the SEQ ID NO: 4.

Another aspect of the present invention provides an environmental stress tolerant transgenic plant cell, plant or plant part which expresses environmental stress responsive protein ferritin, wherein said plant comprising the nucleic acid having at least 90% identity with the nucleotide sequence as set forth in SEQ ID NO: 3.

Yet another aspect of the present invention relates to dehydration stress tolerant transgenic plant cell, plant or plant part which expresses environmental stress responsive protein ferritin, wherein said plant comprising the nucleic acid having at least 90% identity with the nucleotide sequence as set forth in SEQ ID NO: 3.

Yet another aspect of the present invention relates to transgenic plant cell, plant or plant part with high iron content by the over-expression of environmental stress responsive protein ferritin, wherein said plant comprising the nucleic acid having at least 90% identity with the nucleotide sequence as set forth in SEQ ID NO: 3.

A. An aliquot of 100 µg of protein, each from ECM, chloroplast and nuclear fractions were separated by 12.5% SDS PAGE and B-C. 125 µg of protein was resolved by 2-DE. The 1-D (A) and 2-D gels (C) were electroblotted onto Hybond-C membrane and CaFer1 was detected with rabbit polyclonal human anti-ferritin antibody. The arrowheads indicate the position of CaFer1 protein. The corresponding spots in 2-DE gel image (B) and the 2-D immunoblot (C) are indicated.

D-F. Immunolocalisation of CaFer1 gene family protein in organellar compartments of chickpea. Transmission electron micrographs showing labeling with (D) pre-immune sera and E-F. Rabbit polyclonal human anti-ferritin antibody followed by 15 nm gold-conjugated goat anti rabbit IgG secondary antibody. Immunolocalisation of CaFer1 in ECM and chloroplast is indicated by arrowheads (CW-cell wall, Cy-cytoplasm and Ch-chloroplast).

Figure 3:
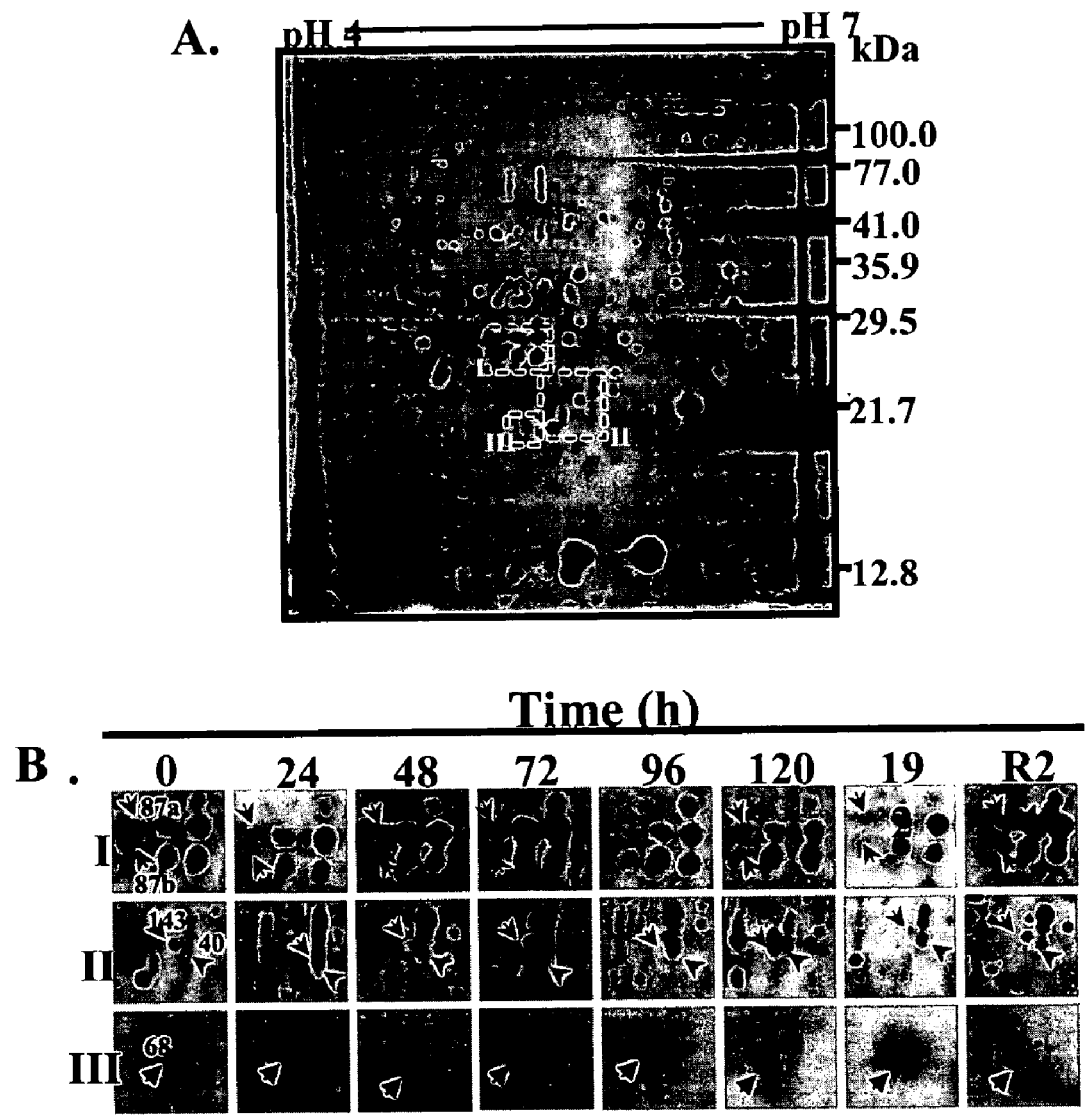

FIG. 3 shows a dehydration-responsive changes in chickpea ECM proteome analyzed by 2-DE. The boxed regions represent the zoomed in gel sections. B. The differential display of ferritin spots are indicated by arrows.

Figure 4:
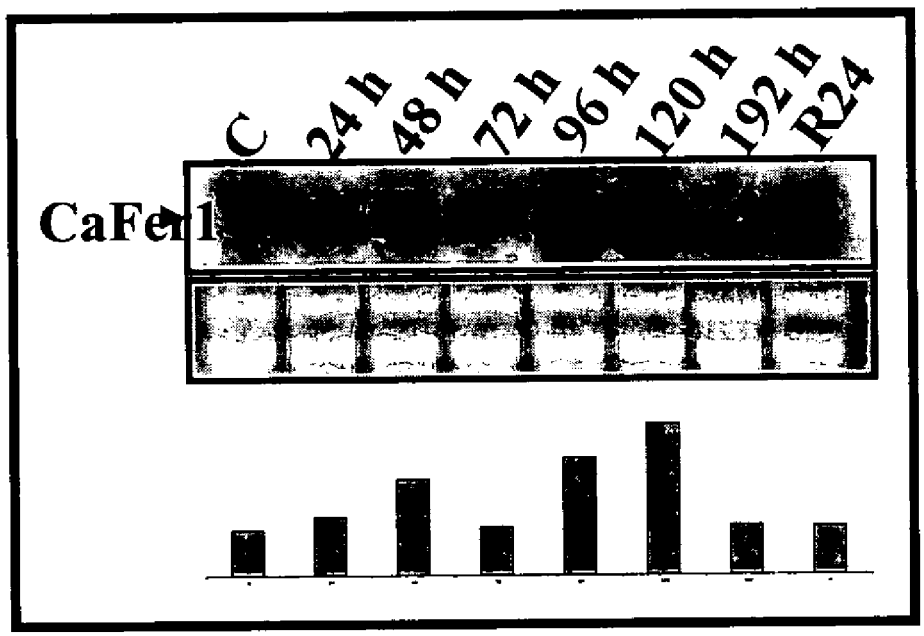
Figure 4:
Figure 5:
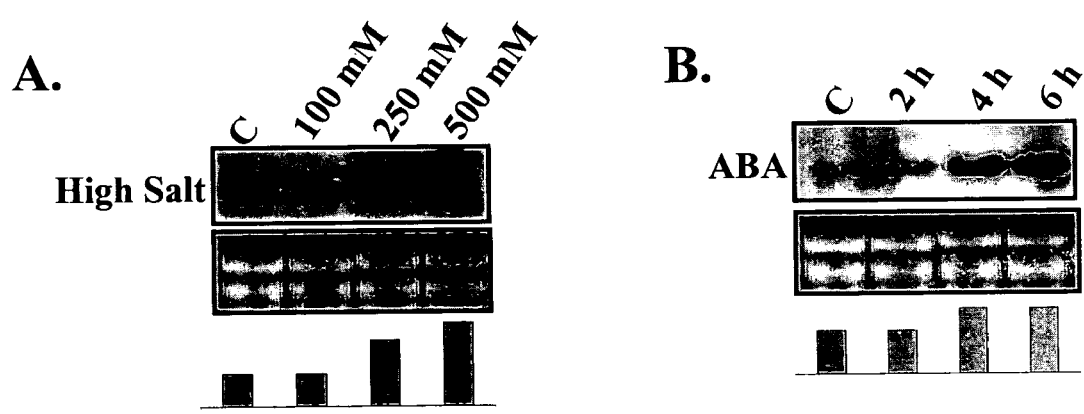

FIG. 4 shows A. RNA analysis of CaFer1 gene expression in chickpea under dehydration; B. ECM proteins prepared from chickpea seedlings were subjected onto 12.5% PAGE and immunoblotting with the rabbit anti-CaFer1 antibody. The lanes are represented by various time points under dehydration, FIG. 5 shows A. Northern blot showing expression of CaFer1 under various concentrations of NaCl; B. Northern blot showing the expression of ferritin at various time points after 100 µM ABA treatment.

Figure 6:
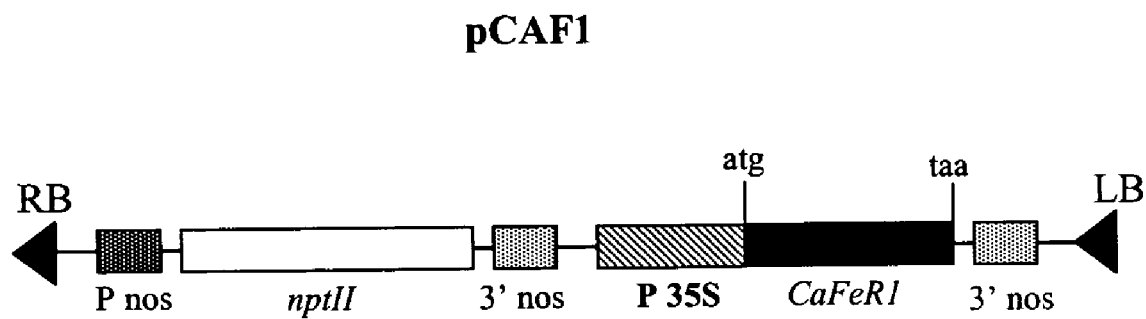

FIG. 6 shows Schematic representation of plant expression plasmid pCAF1 containing CaFeR1 coding sequence.

DETAILED DESCRIPTION OF THE INVENTION

The present invention relates to environmental stress responsive protein ferritin (CaFer1) from chickpea. The invention further relates to the ECM-localized ferritin protein CaFer1, identification, isolation and cloning of the gene encoding same from chickpea and its multifunctional role in nutrient uptake, storage and stress tolerance.

In addition, the invention relates to a recombinant molecule comprising the CaFer1 coding sequence and to a host cell transformed therewith. Further, the invention relates to a method for producing transgenic plants expressing the said CaFer1.

The present invention relates to environmental stress responsive protein ferritin (SEQ ID NO: 4) (CaFer1) of chickpea. The invention further relates to identification, isolation and cloning of ECM-localized ferritin (CaFer1) of chickpea and its multifunctional role in nutrient uptake, storage and stress tolerance. The present invention also provides the method of transformation of plants with the ferritin (CaFer1) from chickpea (SEQ ID NO: 3).

An ECM proteome map was developed for a food legume, chickpea, to identify ECM-associated novel protein/s and to analyze their cellular function. Classical 2-DE technique followed by LC-MS/MS was used to identify a total of 153 ECM proteins.

The Applicant reports here evidence for an ECM-localized, stress-responsive ferritin (CaFer1) hitherto undiscovered, with an apparent molecular mass of approximately 28-29 kDa (corresponding to that of ferritin subunit). The ECM-localization of CaFer1 was determined by immunodetection and also confirmed by immunocytochemistry experiments on cross-section of chickpea tissue.

It was found that the ECM-associated CaFer1 plays a critical role in cellular defense mechanism. In addition, ferritin, being a major form of endogenous iron in food legumes is useful as a novel and natural alternative for iron supplement strategies where effectiveness is limited by acceptability, cost, and undesirable side effects. The ECM resident CaFer1 plays critical role in stress tolerance besides its conventional role in iron uptake, transport, and storage. Plants under stress tend to maintain a balance between the defensive components and the level of reactive oxygen intermediate (ROI), which is crucial for protection against oxidative damage. This balance together with sequestering of intracellular iron is important to prevent stress induced lipid peroxidation.

A proteomic approach was used to identify dehydration responsive ECM proteins in a food legume, chickpea. Dehydration responsive temporal changes of ECM proteins were monitored using two-dimensional electrophoresis (2-DE). Nearly, 200 spots showed variance at 95% significance level statistically. ESI-MS/MS led to the identification of 134 differentially expressed proteins, including well known and novel dehydration responsive proteins (DRPs). Among the dehydration-responsive ECM proteins, at least nine spots that increased upon dehydration treatment were identified as the designated chickpea ferritin (CaFer1).

The dehydration responsive differential expression of ECM proteome in chickpea revealed ferritin (CaFer1) as one of the novel DRP candidates that might be involved in stress tolerance. The 2-DE analyses showed a total of five differential spots for ferritin. The role of ferritin in stress tolerance was elucidated by expression analysis both in terms of transcript and protein levels under dehydration. Further, CaFer1 was found to be responsive to both salt stress and ABA treatment suggesting that it is involved in osmotic stress responsive pathway. Classically, iron storage protein, ferritin, is reported to be present in the plastids. Interestingly, there are reports of ferritins being localized to other cellular compartments such as mitochondria and nucleus (Harrison and Arosio, 1996; Kwok and Richardson, 2004).

The present invention for the first time, provide evidence of stress responsive ECM localized ferritin in chickpea. It is likely that CaFer1 plays differential role in stress tolerance such as environmental stress tolerance besides its classical role in iron storage.

The present invention relates to dehydration-responsive extra cellular matrix (ECM) protein ferritin 1 (CaFer1) of chickpea. The invention further relates to identification, isolation and cloning of ECM-localized ferritin 1 (CaFer1) of chickpea and its multifunctional role in nutrient uptake, storage and stress tolerance.

One embodiment of the present invention provides an isolated polypeptide having environmental stress responsive activity comprising the amino acid sequence as set forth in the SEQ ID NO: 4.

Another embodiment of the present invention provides a nucleotide sequence having at least 90% identity with the nucleotide sequence as set forth in SEQ ID NO: 3, wherein said nucleotide sequence encodes for the polypeptide having the amino acid sequence as set forth in the SEQ ID NO: 4.

Yet another embodiment of the present invention provides an isolated nucleic acid having at least 300 contiguous nucleotide sequence as set forth in SEQ ID NO: 3, wherein said nucleotide sequence encodes a polypeptide comprising the amino acid sequence as set forth in the SEQ ID NO: 4.

Still yet another embodiment of the present invention provides a recombinant vector comprising the nucleic acid having nucleotide sequence having at least 90% identity with the nucleotide sequence as set forth in SEQ ID NO: 3.

In one embodiment, the present invention provides a recombinant vector comprising the nucleic acid having nucleotide sequence as set forth in SEQ ID NO: 3.

In another embodiment, the present invention provides recombinant host cell such as *E. coli* and *Agrobacterium*, yeast cells comprising the recombinant vectors having the nucleotide sequence having at least 90% identity with the nucleotide sequence as set forth in SEQ ID NO: 3.

In yet another embodiment, the present invention provides recombinant host cell such as *E. coli* and *Agrobacterium*, yeast cells comprising the recombinant vectors having the nucleotide sequence as set forth in SEQ ID NO: 3.

In another embodiment, the present invention provides a method for producing a transformed plant cell, plant or plant part expressing environmental stress responsive protein ferritin, said method comprising transforming a plant cell, plant or plant part with a nucleotide sequence having at least 90% identity with the nucleotide sequence as set forth in SEQ ID NO: 3, wherein said nucleotide sequence encodes ferritin protein comprising amino acid sequence as set forth in the SEQ ID NO: 4.

Further embodiment of the present invention provides a method for producing a transformed plant cell, plant or plant part expressing environmental stress responsive protein ferritin, said method comprising transforming a plant cell, plant or plant part with a nucleotide sequence having the nucleotide sequence as set forth in SEQ ID NO: 3, wherein said nucleotide sequence encodes ferritin protein comprising amino acid sequence as set forth in the SEQ ID NO: 4.

In one embodiment, the present invention provides the transformed plant cell, plant or plant part tolerant to an environmental stress, wherein the environmental stress is selected from a group consisting of dehydration stress, salt stress, oxidative stress, low temperature stress and phytohormone stress.

In one embodiment, the present invention provides a method for producing a transformed plant cell, plant or plant part having high iron content, said method comprising transforming a plant cell, plant or plant part with a nucleotide sequence having at least 90% identity with the nucleotide sequence as set forth in SEQ ID NO: 3, wherein said nucleotide sequence encodes ferritin protein comprising amino acid sequence as set forth in the SEQ ID NO: 4.

In another embodiment, the present invention provides a method for producing a transformed plant cell, plant or plant part having high iron content, said method comprising transforming a plant cell, plant or plant part with a nucleotide sequence having the nucleotide sequence as set forth in SEQ ID NO: 3, wherein said nucleotide sequence encodes ferritin protein comprising amino acid sequence as set forth in the SEQ ID NO: 4.

The present invention also provides dehydration stress tolerant transformed plant cell, plant or plant part comprising the isolated nucleotide sequence coding for ferritin protein comprising amino acid sequence as set forth in the SEQ ID NO: 4.

The present invention also provides salt stress tolerant transformed plant cell, plant or plant part comprising the isolated nucleotide sequence coding for ferritin protein comprising amino acid sequence as set forth in the SEQ ID NO: 4.

The present invention also provides oxidative stress tolerant transformed plant cell, plant or plant part comprising the isolated nucleotide sequence coding for ferritin protein comprising amino acid sequence as set forth in the SEQ ID NO: 4.

The present invention provides the transformed plant cell, plant or plant part, comprising the isolated nucleotide sequence coding for ferritin protein comprising amino acid sequence as set forth in the SEQ ID NO: 4, wherein the plant is dicot and monocot.

The present invention provides the transformed plant cell, plant or plant part, comprising the isolated nucleotide sequence coding for ferritin protein comprising amino acid sequence as set forth in the SEQ ID NO: 4, wherein the plant is selected from a group consisting of cereals, legumes, fruits and vegetables.

The present invention provides the transformed plant cell, plant or plant part, comprising the isolated nucleotide sequence coding for ferritin protein comprising amino acid sequence as set forth in the SEQ ID NO: 4, wherein the monocot is selected from a group consisting of rice, wheat, barley, rye, corn, sorghum, and sugarcane.

The present invention provides the transformed plant cell, plant or plant part, comprising the isolated nucleotide sequence coding for ferritin protein comprising amino acid sequence as set forth in the SEQ ID NO: 4, wherein the dicot is selected from a group consisting of potato, carrot, sweet potato, cassaya, bean, chickpea, pigeonpea, pea, grasspea, cabbage, cauliflower, eggplant, soybean, tomato.

Another embodiment of the present invention relates to an environmental stress tolerant transgenic plant cell, plant or plant part which expresses environmental stress responsive protein ferritin, wherein said plant comprising the nucleic acid having at least 90% identity with the nucleotide sequence as set forth in SEQ ID NO: 3.

Yet another embodiment of the present invention relates to a dehydration stress tolerant transgenic plant cell, plant or plant part which expresses environmental stress responsive protein ferritin, wherein said plant comprising the nucleic acid having at least 90% identity with the nucleotide sequence as set forth in SEQ ID NO: 3.

Yet another embodiment of the present invention relates to transgenic plant cell, plant or plant part with high iron content by the over-expression of environmental stress responsive protein ferritin, wherein said plant comprising the nucleic acid having at least 90% identity with the nucleotide sequence as set forth in SEQ ID NO: 3.

The present invention further provides a transgenic seed tolerant to environmental stress, wherein the seed contains the isolated nucleic acid encoding environmental stress responsive protein ferritin.

The present invention further provides a transgenic seed tolerant to dehydration stress, wherein the seed contains the isolated nucleic acid encoding environmental stress responsive protein ferritin.

The present invention further provides a transgenic seed over-accumulating iron, wherein the seed contains the isolated nucleic acid encoding environmental stress responsive protein ferritin.

The present invention further provides a transgenic progeny plant tolerant to environmental stress comprising the isolated nucleic acid encoding environmental stress responsive protein ferritin.

The present invention further provides a transgenic progeny plant tolerant to dehydration stress comprising the isolated nucleic acid encoding environmental stress responsive protein ferritin.

The present invention further provides a transgenic progeny plant over-accumulating iron comprising the isolated nucleic acid encoding environmental stress responsive protein ferritin.

Plant Growth, Maintenance, and Application of Dehydration

Chickpea (*Cicer aritienum* L.) seedlings were grown in pots containing a mixture of soil and soilrite (2:1, w/w) in an environmentally controlled growth room and maintained at 25±2° C., 50±5% relative humidity under 16 h photoperiod (270 µmol m$^{-2}$ s$^{-1}$ light intensity). A gradual dehydration condition was applied on the plants by withdrawing water after 21 d and tissues were harvested at every 24 h up to 192 h. The seedlings were then re-watered allowing complete recovery for 24 h (R24 h) and tissues were harvested. The harvested tissues were instantly frozen in liquid nitrogen and stored at −80° C. unless described otherwise.

Isolation of ECM Fraction and Electron Microscopy

The ECM-enriched fraction was isolated as described (Stuart and Varner, 1980; Averyhart-Fullard et al., 1988) with few modifications. In brief, the tissues were ground to powder in liquid nitrogen with 0.3% (w/w) polyvinylpolypyrollidone (PVPP) and transferred to an open-mouthed 50 ml centrifuge tube. Immediately, tissue powder was homogenized in homogenizing buffer (5 mM K$_3$PO$_4$, pH 6.0; 5 mM DTT, 1 mM PMSF) for 1 to 2 min. The cell wall fraction was recovered by differential centrifugation at 1000 g for 5 min at 4° C. The pellet thus obtained was washed ten times with excess deionized water and fixed with Karnovsky's fixative (2% (v/v) paraformaldehyde/2.5% (v/v) glutaraldehyde] overnight at 4° C. It was then washed in 0.1 M phosphate buffer and treated with 1% osmium tetroxide. The fraction was dehydrated sequentially in acetone and embedded in epoxy resin. Ultra thin sections (70 nm) were made, stained for 10 min each with uranyl acetate and lead citrate consecutively and analyzed by transmission electron micrography. (Morgagni 268D).

Figure 1:
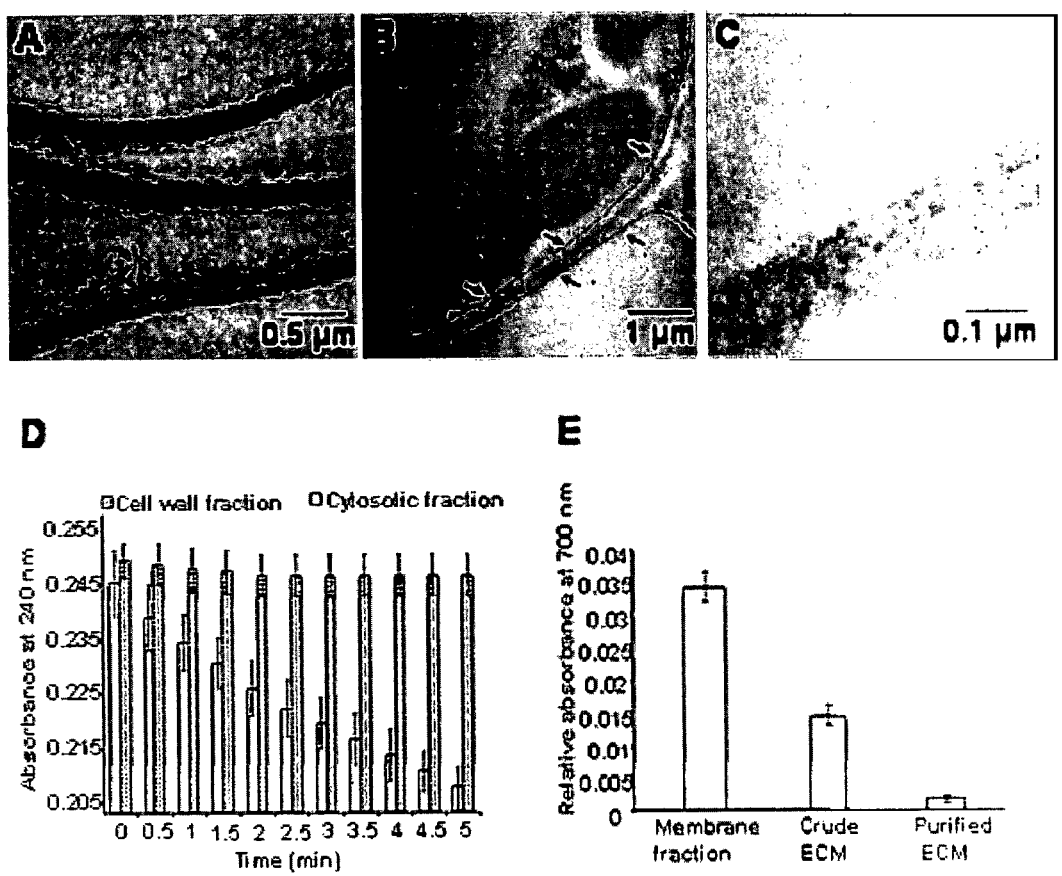
FIG. 1 shows Electron micrograph of
A. Purified ECM fraction
B. PTA stained section of chickpea leaflet showing plasma membrane specificity of the staining as indicated by arrowheads
C. PTA stained section of purified ECM. The bar on the micrographs indicates the extent of resolution
D. Determination of catalase specific activity in chickpea ECM and cytosolic fraction. The cytosolic fraction prepared from chickpea tissue for catalase activity was used as positive control
E. Determination of vanadate inhibited $H^+$ ATPase activity in chickpea ECM and plasma membrane fraction. The plasma membrane fraction of chickpea was used as positive control

A 2-DE map of the differentially expressed chickpea ECM proteome was developed from ECM-enriched fraction. The microscopy results showed that the ECM fraction was free of plasma membranes or other ultrastructural cytoplasmic organelles and that there were no intact cells, which had escaped breakage during processing (FIG. 1A). To compliment the electron microscopic observation, a plasma membrane specific PTA staining of isolated ECM fraction along with tissue-section was carried out (FIGS. 1B and 1C). While the plasma membrane showed distinct PTA staining in tissue section, the purified ECM did not show any stain. The ECM-enriched fraction was evaluated further by organellar-specific marker enzyme analysis; catalase activity as cytosolic while vanadate inhibited H$^+$ ATPase, for the plasma membrane contamination (Larsson et al., 1994). As shown in FIG. 1D, ECM proteins did not show any significant catalase activity, whereas the cytosolic proteins showed high catalase activity. The plasma membrane fraction displayed a high activity of the vanadate inhibited H$^+$ ATPase as shown in FIG. 1E. By contrast, the crude cell wall fraction (ECM pellet before washing) showed a little amount of enzyme activity while the purified ECM fraction did not show any activity. These results altogether suggest that cytosolic and plasma membrane contaminations of the ECM, if any, were beyond detectable limit.

ECM Protein Extraction and Quantification

The ECM-enriched fraction was suspended in three volumes (w/v) of extraction buffer (200 mM CaCl$_2$, 5 mM DTT, 1 mM PMSF, 0.3% (w/w) PVPP] and extracted on a shaking platform for 45 min at 4° C. Proteins were separated from the insoluble ECM fraction by centrifugation (10,000×g) for 10 min at 4° C. and filtered through 0.45 µm filter. The filtrate was concentrated using Centricon YM3 and then dialyzed overnight against 1000 volumes of deionized water with one change. The concentration of protein extract was determined by Bradford assay (Bio-Rad, CA, USA).

Enzyme Assay

The catalase enzyme assay was performed using 10 µg of organellar proteins prepared by standard procedures. The reaction mixture was prepared by adding 50 µl, of protein extract to 940 µl, of 70 mM potassium phosphate buffer (pH 7.5). Reaction was started by addition of 10 µL of H$_2$O$_2$ (3% v/v) and the decrease in absorbance at 240 nm was monitored for 5 min. Baseline correction was done by subtracting the absorbance taken without addition of H$_2$O$_2$. The assay was performed in triplicates and the absorbance values obtained were plotted against time.

The vanadate inhibited H$^+$ ATPase activity was determined for ECM and plasma membrane fraction with 20 µg of protein in 120 µL of assay buffer The assay was performed in presence and absence of 0.1 orthovanadate, freshly prepared and boiled in buffer prior to addition of 0.05% triton X-100. The assay was performed in presence of a detergent to expose all hidden sites for the cell wall bound plasma membrane, if any. The reaction was initiated by addition of ATP and was incubated at 37° C. for 30 min. Blanks lacking MgSO$_4$ were run in parallel (Larsson et al., 1994) and the released inorganic phosphate was determined (Ames, 1966). The relative activity of the enzyme was calculated by taking the difference between the absorbance at 700 nm in absence and presence of orthovanadate.

Phosphotungstic Acid Staining (PTA)

PTA at low pH can be used to stain specifically the plasma membrane in thin sections for electron microscopy (Larsson et al., 1994). Thin sections of glutarladehyde and osmium tetroxide fixed purified ECM fraction were lifted on nickel grids and destained by placing a droplet of 1% (w/v) periodate, pH 3.0 for 15 min at 20° C. and rinsed for 5 min with distilled water. The grid was then incubated in 1% PTA, pH 3.0 for 10 min at 37° C. and rinsed with 1 mM HCl. The specificity of the PTA staining to plasma membrane was checked on a section of leaf tissue.

2-Dimensional Gel Electrophoresis

The ECM proteins were precipitated with 100% acetone after boiling in dilution buffer (Hurkman and Tanaka, 1986). Protein pellets were washed twice with 80% acetone, air dried and resuspended in 2-D rehydration buffer [8 M urea, 2 M thiourea, 4% (w/v) CHAPS, 20 mM DTT, 0.5% (v/v) pharmalyte and 0.05% (w/v) bromophenol blue]. Isoelectric focusing was carried out with 300 µg protein in 350 µL 2-D rehydration buffer for 18 cm pre-cast gel strips (pH 4-7). Electrofocusing was performed using IPGphor system (Amersham Biosciences, Bucks, UK) at 20° C. for 40,000 Vh for 18 cm gels. The focused strips were subjected to reduction with 1% (w/v) DTT in 10 mL of equilibration buffer [6 M urea, 50 mM Tris-HCl (pH 8.8), 30% (v/v) glycerol and 2% (w/v) SDS], followed by alkylation with 2.5% (w/v) iodoacetamide in the same buffer. The strips were then loaded on top of 12.5% polyacrylamide gels for SDS-PAGE. The electrophoresed proteins were stained with silver stain plus kit and images were digitized with a FluorS equipped with a 12-bit camera (Bio-Rad, CA, USA).

2-D Gel Electrophoresis and Protein Identification

A 2D gel of ECM proteins revealed approximately 450 protein spots evenly distributed between pH 4 and 7 and molecular masses of 14 to 120 kDa. The gel images were analyzed by the PD Quest software, followed by filtering of low-quality data, girding the spots, and determination of expected molecular mass and pI of each spot. A total of 376 spots survived the filtering process, which were numbered as CaE-1 to CaE-376, [the alphabets identify the organism (*Cicer arietinum*) and the subcellular organelle (ECM) from which the proteome map has been made, whereas the numerals indicate the spot numbers].

To identify dehydration responsive ECM proteins, a comparative proteomic analysis was conducted. ECM proteins were isolated from control and dehydration treated chickpea seedlings and subjected to 2-D gel electrophoresis. The DRPs (dehydration responsive proteins) were identified by MS-MS analysis, wherein five differential spots corresponding to Ferritin were identified (FIG. 3).

The dynamics of the chickpea ECM proteome was studied under progressive dehydration conditions. Of the protein spots displaying greater than 2.5-fold upregulation or downregulation, 153 proteins were subjected to identification with LC-MS/MS. Among the dehydration-responsive components, 5 spots (spot numbers 87a, 87b, 40, 68 and 143) representing CaFer, were initially selected for further characterization. Four additional spots (55, 70, 71, and 74b) were identified as the members of the ferritin gene family that have the theoretical pI values between 5.2 and 5.6 and the peptide masses from the spectra matched that of Ferritin in the database search, indicating that all the spots represent CaFer proteins. CaFer1 is an interesting ECM component for the following reasons: (1) ferritin participates in essential cellular processes in animal cells (Beard and Connor, 2003; Casanueva and Viteri, 2003; Ferreira et al., 2000); (2) plant ferritin gene is regulated by a complex interplay of transcriptional and posttranscriptional mechanism, involving cellular relays such as hormones, and oxidative steps (Briat et al., 1999); and (3) its localization in the ECM is suggestive of its role in plant defense against environmental stress.

Protein Identification Using MS/MS

Electrospray ion trap LC-MS/MS analysis was done using Q-Star Pulsar i (Applied Biosystems) or LCQ DECA XP Plus (Finnigan). The spectra were analyzed either by Mascot sequence matching software (www.matrixscience.com) and the Viridiplantae (green plants) database or Sequest Algorithm searching against all organism databases.

Immunoblotting

Immunoblotting was done by resolving the protein on a uniform 12.5% SDS PAGE and then electrotransferring onto nitrocellulose membrane at 150 mA for 2 h. The membranes were probed with rabbit polyclonal human anti-ferritin antibody diluted to 1:5000 in Tris-buffered saline (TBS). Antibody bound proteins were detected by incubation with alkaline phosphatase conjugated anti-rabbit IgG as secondary antibody.

Immunoelectron Microscopy

Chickpea leaflet sections were fixed in 4% paraformaldehyde and 1% glutaraldehyde in 0.1 M PBS (pH 7.2), dehydrated over grades of ethanol at 4° C., and embedded in LR-white resin (Hard). Thin sections (60-90 nm) lifted onto 400 mesh nickel grids was blocked with 3% BSA in TBS for 1 h at room temperature. Immunolabelling was done with polyclonal rabbit anti-human ferritin antibody diluted to 1:1000 in TBS. The grids were incubated with AuroProbeEM GAR G15 at a dilution of 1:50 in TBS containing 0.5% Tween 20 for 1 h at room temperature. Grids were post-fixed in 2.5% glutaraldehyde in 0.1 M PBS (pH 7.2) for 10 min and stained with 2% aqueous uranyl acetate for 20 min at room temperature and micrographed with a transmission electron microscope.

Immunodetection and Localization of CaFer1

Figure 2:
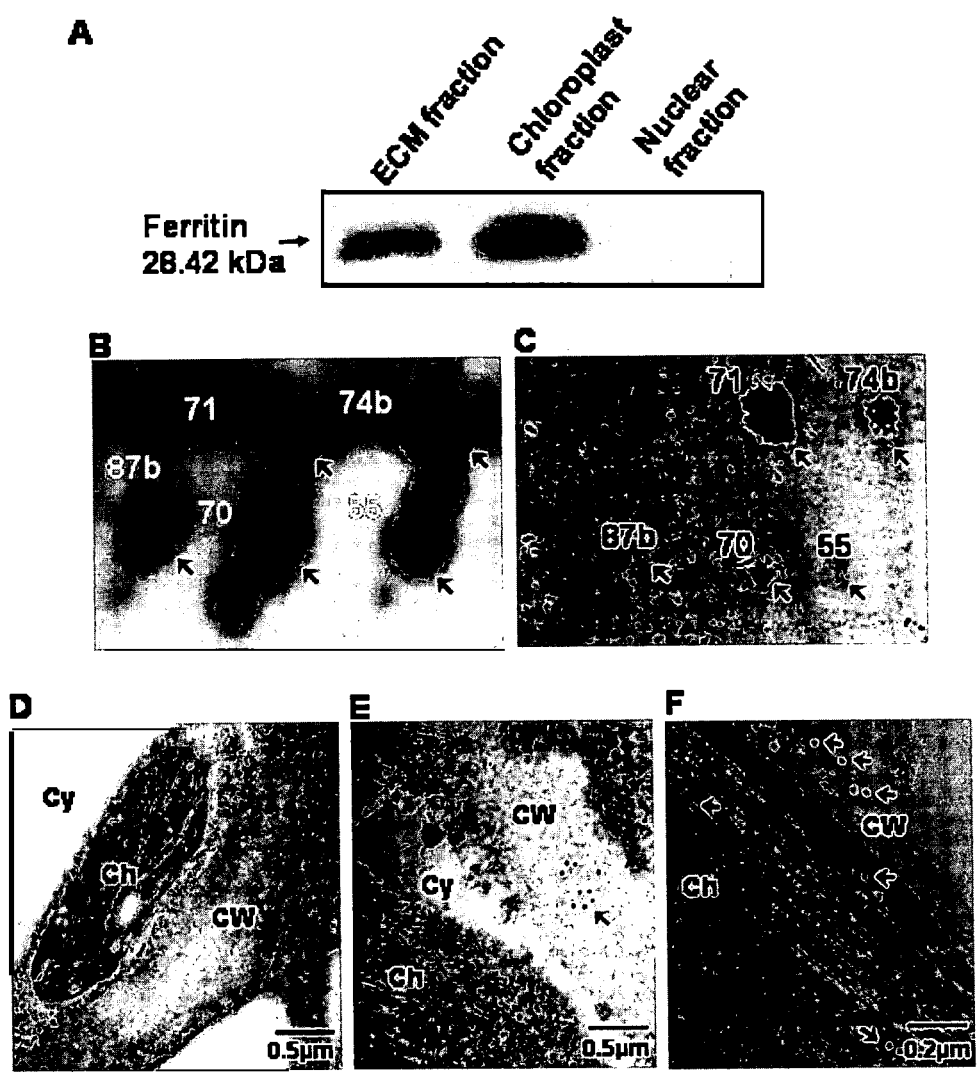
FIG. 2 shows immunodetection of CaFer1 gene family protein in chickpea ECM fraction.

The presence of CaFer1 in chickpea ECM was investigated by immunoblot analysis of proteins isolated from ECM along with chloroplast and nuclear fractions using CaFer1 specific antibody. CaFer1 was found in the ECM as well as in the chloroplast fractions, but not in the nuclear fraction (FIG. 2A). The result suggests that in chickpea, CaFer1 is present both in ECM and chloroplast. As many as eight spots were identified including a cluster of five (FIG. 2B) in 2-DE. To confirm their identity, a 2-D immunoblot of the protein spots was carried out using ferritin-specific antibody. At least four spots in the designated cluster showed CaFer1 specificity (FIG. 2C). Spot 87b did not show any signal and this may be attributed to the changes in epitope caused by post translational modification of the CaFer1 isoforms.

To further confirm the presence of CaFer family members in the ECM, the subcellular localization of CaFer1 was studied by immunocytochemistry. In consistence with the immunoblot results, CaFer1 was found in ECM and chloroplasts (FIG. 2D-2F). These results confirm CaFer1 as ECM residents besides their presence in classical subcellular compartments, the chloroplast.

Cloning of ECM-Localized Ferritin

Proteomic analysis of the chickpea ECM revealed three sequence tags for CaFer1. The conserved MS sequence (ESSEEREHAEKL) was used to design the ferritin gene specific primer (5' gAAgAAAgAgAgCATgCTg3'-SEQ ID NO: 1). The partial clone (0.6 Kb) was obtained by 3'-RACE technique using chickpea RNA. The clone was sequenced and its identity was confirmed by database BLAST. This partial clone was used to screen a chickpea cDNA library to obtain the full-length CaFer1.

Nucleotide sequence of the partial clone of CaFer1 is provided in SEQ ID NO: 2. The clone was sequenced and the identity was confirmed by BLAST search.

Full-Length cDNA Clone for Ferritin

A cDNA library was made with RNA isolated and pooled from dehydration stressed chickpea seedlings during 192 h of stress followed by a recovery period of 24 h. The library was screened using the $^{32}$P-labeled partial ferritin cDNA as probe (SEQ ID NO: 2). A full-length ferritin clone (1078 bp) was obtained and designated as CaFer1 (SEQ ID NO: 3). The full-length sequence of ferritin gene was analyzed in silico and a 765 by long ORF with 112 by of 5' UTR and 201 by of 3' UTR was obtained for ferritin. The gene sequence was translated in six frames to get the protein sequence for ferritin. The right translation frame was identified by matching the sequence tags obtained for the protein spots in 2-D gel. The protein size was calculated to be around 28 kDa as determined by 2-D gel.

Expression of CaFer1 in Response to Dehydration

In order to check the expression level of CaFer1 under dehydration, the difference in the transcript level was analyzed by Northern blot analyses. The level of expression of ferritin increased at 48 h but showed a marginal drop at 72 h under dehydration (FIG. 4A). A strong induction of CaFer1 transcript was observed during 96-120 h, which returned to basal level 120 h of dehydration. The transcript levels were co-related with the levels of protein expression as indicated by immunoblot analysis under dehydration at various time points. A constant induction in the protein levels was observed between 48-120 h (FIG. 4B), which corroborates with the differential display of ferritin observed in 2-DE.

Expression of CaFer1 in Response to Other Environmental Stresses

The level of CaFer1 expression was further investigated by Northern blot analysis under high salt and ABA treatment. The CaFer1 transcripts were induced by high salt (250 and 500 mM) while no induction was observed at 100 mM salt concentration (FIG. 5A). Further, CaFer1 expression level was induced by ABA application after 4 h of stress treatment (FIG. 5B). The induced expression of CaFer1 under high salt and ABA treatment beside dehydration suggest that ferritin may participate in the ABA dependent signaling in stress responsive pathway.

Stress Treatments

The chickpea seedlings were grown as described above. A gradual dehydration condition was applied on the 3-week-old seedlings by withdrawing water and tissues were harvested at every 24 h up to 192 h. The pots were then re-watered allowing complete recovery for 24 h and tissues were harvested. Salt stress was applied on pot grown three-week-old chickpea seedlings. The plants were supplied with half-Hoagland's medium everyday till three weeks followed stress treatment by different concentrations of NaCl (100, 250, and 500 µM) in the same medium the next day. The tissues under stress were harvested 24 h after the treatment. ABA stress was given by spraying 100 µM solution of ABA on the leaves of three-week-old chickpea seedlings and tissues were harvested every 2 h after stress treatment for 6 h. The harvested tissues were instantly frozen in liquid nitrogen and stored at −80° C.

RNA Blot Hybridization

Total RNA was extracted from control and dehydration treated chickpea seedlings using TriPure Isolation Reagent (Roche Diagnostics, Indianapolis). Using formaldehyde as a denaturant, 30 µg of total RNA was subjected to gel electrophoresis (1.2%). Ethidium bromide staining under UV light was used to ascertain equal gel loading and efficient transfer to nylon membrane. [$\alpha$-$^{32}$P]CTP labeled partial ferritin cDNA was used as the probe. The membrane was hybridized in 50% formamide (w/v) hybridization buffer at 42° C. for 18 h. Washing was as follows: 2×SSC at room temperature for 5 min, 2×SSC and 0.1% (w/v) SDS at room temperature for 5 min; 0.1×SSC and 0.5% (w/v) SDS at 42° C. for 5-10 min. The film was exposed to KODAK X-ray film and autoradiographed.

RNA-Interference Based Ferritin Gene Silencing in *Arabidopsis*

*A. thaliana* ferritin gene family has four members, viz, AtFer1-4. The entire cDNA sequence of CaFer1 was aligned with paralogs from *Arabidopsis* using ClustalW, which recognized a 300 by homologous region. Primers, Forward 5'GGGGACAAGTTTGTACAAAAAAGCAG-GCTCAACCCACGCTTTGTATGCATATTTCG 3' (SEQ ID NO: 5) and Reverse 5' GGG GAC CAC TTT GTACAA-GAAAGCTGGGT CTCCCCAATGAAAGAGCCAACTCC 3' (SEQ ID NO: 6) were designed in order to amplify this homologous region. The amplified product was cloned into pFGC5941 using the method known in the art yielding the plasmid pCAF1i and maintained in DB3.1 strain of *E. coli*. The plasmid pCAF1i containing the RNAi cassette was isolated and transformed into *Agrobacterium* strain GV3101 by electroporation and eventually into *Arabidopsis* (Co10 background). The F1 seeds obtained were selected in MS media supplemented with BASTA (4-glufosinate ammonium; Crescent Chemicals, New Jersey, USA). This F1 population was selfed to obtain the homozygous F2 population which was used to analyze for phenotype, if any, indicative of ferritin gene function under stress. A total of 32 RNAi plants were selected and one of the putative plants was taken for further characterization.

Phenotypic Screening of atferi Plants Under Different Environmental Stresses

To assess the functional role of ferritin under different environmental stresses, the seed germination assay of atferi plants was carried out.

Sensitivity of atferi Plants to $H_2O_2$

The atferi seeds were allowed to germinate on MS media supplemented with 20 mM $H_2O_2$. The seeds of ferritin RNAi plants did not show any germination as compared to Co10 control seeds which showed a 100% rate of germination. The sensitivity of ferritin RNAi plants to $H_2O_2$ is corroborative with earlier findings (Deak et al., 1999) and it can be inferred that ferritin plays an important role in oxidative stress tolerance.

Sensitivity of atferi Plants to Osmotic Stress

In order to confirm the role of ferritin under osmotic stress, germination experiment was done by creating a water potential of $0.5\psi$ using PEG. The atferi seeds failed to germinate under osmotically challenged conditions as compared to 90% germination for Co10 seeds. It is thus suggested that ferritin may be directly involved in dehydration tolerance mechanisms in plants. Also, the induced expression of ferritin under dehydration in chickpea indicates its possible role in osmotic stress tolerance mechanism.

Sensitivity of atferi Plants to NaCl

There are many reports on crosstalk between high salt and dehydration stress pathways (Shinozaki and Shinozaki, 1997) in plants. The osmotic stress is induced under salt stress as there is decreased availability of water due to accumulation of ions. The atferi seeds were germinated on MS media supplemented with 150 mM NaCl along with the control Co10 seeds. The seeds did not germinate on the salt supplemented media as compared to Co10 seeds which showed 100% germination under identical conditions. These results suggest that ferritin may be involved in salt stress response.

Sensitivity of atferi Plants to ABA Application

Earlier studies suggest that phytohormone ABA plays a crucial role in dehydration and salt stress response (Shinozaki and Yamaguchi-Shinozaki, 2000). To test this hypothesis, germination assay of atferi seeds was carried out in MS media containing 1 µM ABA. aba-2 are known to be sensitive to ABA and thus were used as negative control in this experiment. The atferi seeds did not germinate in the ABA supplemented medium, however, Co10 seeds germinated. The aba-2 showed defective, germination as the growth of the plant was impaired after radicals emerged. The results suggest that involvement of ferritin in dehydration and salt stress responsive pathway is presumably mediated by ABA.

Construction of Plant Expression Vector for CaFeR1

The basic plasmid pCaFer1 was constructed by PCR amplification of CaFeR1 coding region and cloning into pGEMT easy vector (Promega). In order to express CaFeR1 in plants, the full length cDNA was subcloned in a binary vector and was named as pCAF1 (FIG. 6). The plasmid construct pCAF1 was mobilized into *Agrobacterium* strain by triparental mating technique (Van Haute et al., 1983) or by standard electroporation method.

Plant Transformation for Over-Expression of CaFer1

Any of the various methods known for introducing foreign genes into plants can be used for insertion of pCaFer1 gene into a host plant. The methodology chosen to accomplish plant transformation with the said gene varies depending on the host plant. By way of example, one well-characterized methodology that would be useful for plant transformation with pCaFer1 gene is *Agrobacterium* mediated transformation.

*Agrobacterium* mediated transformation using the pCAF1 plasmid follows the procedure well-known for this methodology. A gene cassette suitable for expression in plants is introduced into a disarmed strain of *Agrobacterium tumefaciens* as in intermediate host. The CaFer1 gene cassette is introduced into the T-DNA region of a recombinant plasmid containing a selectable marker gene such as a gene encoding for neomycin phosphotransferase II, phosphinothricin acetyl transferase, or the like. This methodology is set forth in many literature publications including Horsch et al, (1985, Science 227: 1229-1231). Various explants like leaf, cotyledons, hypocotyl, and embryo were co-cultivated with the *Agrobac-*

*terium* comprising the environmental stress responsive gene CaFer1 for 2-3 days. The explants were then transferred the selection medium containing cefotaxime. Antibiotics corresponding to the selectable marker gene were included in the plant tissue culture medium to select the transformed tissue.

Plants regenerated from the transformed cells were then analyzed for the presence and expression of the pCaFer1 gene. Immunoassays for CaFer1 protein was carried out to identify individual transformants.

Methods well known in the art such as biolistic transformation can also be used for plant transformation apart from *Agrobacterium* transformation. Examples of types of plants that are not especially suitable for *Agrobacterium*-mediated transformation are legumes and certain cereals. These plants would plainly benefit from plant transformation attempts using biolistic approaches.

Transformation of *Arabidopsis*

*Arabidopsis* (Co10) was transformed with *Agrobacterium* containing the plant expression plasmid, pCAF1 Single colony of *Agrobacterium* strain GV3101 was inoculated in 50 ml YEP medium supplemented with 50 µg/ml rifampicin and 50 µg/ml kanamycin. Culture was incubated at 28° C. with shaking at 200 rpm for 48 h, until the $OD_{600}$ reached 0.8. The floral portions of 4-6 weeks old *Arabidopsis* plants were dipped in the *Agrobacterium* culture for 10 s. The pot was wrapped in saran wrap and kept in dark for 48 h before being maintained in long day condition, 16 h photoperiod. The seeds obtained from these plants (F1) were selfed to generate F2 homozygous plants which were used for further studies.

The knockout mutants of *Arabidopsis* were generated using RNAi based plasmid for CaFer1 gene, pCAF1i by the same methodology mentioned above.

EXAMPLES

It should be understood that the following examples described herein are for illustrative purposes only and that various modifications or changes in light will be suggested to persons skilled in the art and are to be included within the spirit and purview of this application and the scope of the appended claims.

Example 1

Plant Growth, Maintenance, and Application of Dehydration

Chickpea (*Cicer aritienum* L.) seedlings were grown in pots containing a mixture of soil and soilrite (2:1, w/w) in an environmentally controlled growth room and maintained at 25±2° C., 50±5% relative humidity under 16 h photoperiod (270 µmol $m^{-2}$ $s^{-1}$ light intensity): A gradual dehydration condition was applied on the plants by withdrawing water after 21 d and tissues were harvested at every 24 h up to 192 h. The seedlings were then re-watered allowing complete recovery for 24 h (R24 h) and tissues were harvested. The harvested tissues were instantly frozen in liquid nitrogen and stored at −80° C. unless described otherwise.

Isolation of ECM Fraction and Electron Microscopy

The ECM-enriched fraction was isolated as described (Stuart and Varner, 1980; Averyhart-Fullard et al., 1988) with few modifications. In brief, the tissues were ground to powder in liquid nitrogen with 0.3% (w/w) polyvinylpolypyrollidone (PVPP) and transferred to an open-mouthed 50 ml centrifuge tube. Immediately, tissue powder was homogenized in homogenizing buffer (5 mM $K_3PO_4$, pH 6.0; 5 mM DTT, 1 mM PMSF) for 1 to 2 min. The cell wall fraction was recovered by differential centrifugation at 1000 g for 5 min at 4° C. The pellet thus obtained was washed ten times with excess deionized water and fixed with Karnovsky's fixative (2% (v/v) paraformaldehyde/2.5% (v/v) glutaraldehyde] overnight at 4° C. It was then washed in 0.1 M phosphate buffer and treated with 1% osmium tetroxide. The fraction was dehydrated sequentially in acetone and embedded in epoxy resin. Ultra thin sections (70 nm) were made, stained for 10 min each with uranyl acetate and lead citrate consecutively and analyzed by transmission electron micrography (Morgagni 268D).

A 2-DE map of the differentially expressed chickpea ECM proteome was developed from ECM-enriched fraction. The microscopy results showed that the ECM fraction was free of plasma membranes or other ultrastructural cytoplasmic organelles and that there were no intact cells, which had escaped breakage during processing (FIG. 1A). To compliment the electron microscopic observation, a plasma membrane specific PTA staining of isolated ECM fraction along with tissue-section was carried out (FIGS. 1B and 1C). While the plasma membrane showed distinct PTA staining in tissue section, the purified ECM did not show any stain. The ECM-enriched fraction was evaluated further by organellar-specific marker enzyme analysis; catalase activity as cytosolic while vanadate inhibited $H^+$ ATPase, for the plasma membrane contamination (Larsson et al., 1994). As shown in FIG. 1D, ECM proteins did not show any significant catalase activity, whereas the cytosolic proteins showed high catalase activity. The plasma membrane fraction displayed a high activity of the vanadate inhibited $H^+$ ATPase as shown in FIG. 1E. By contrast, the crude cell wall fraction (ECM pellet before washing) showed a little amount of enzyme activity while the purified ECM fraction did not show any activity. These results altogether suggest that cytosolic and plasma membrane contaminations of the ECM, if any, were beyond detectable limit.

Example 2

ECM Protein Extraction and Quantification

The ECM-enriched fraction was suspended in three volumes (w/v) of extraction buffer (200 mM $CaCl_2$, 5 mM DTT, 1 mM PMSF, 0.3% (w/w) PVPP) and extracted on a shaking platform for 45 min at 4° C. Proteins were separated from the insoluble ECM fraction by centrifugation (10,000×g) for 10 min at 4° C. and filtered through 0.45 µm filter. The filtrate was concentrated using Centricon YM3 and then dialyzed overnight against 1000 volumes of deionized water with one change. The concentration of protein extract was determined by Bradford assay.

Enzyme Assay

The catalase enzyme assay was performed using 10 µg of organellar proteins prepared by standard procedures. The reaction mixture was prepared by adding 50 µL of protein extract to 940 µL of 70 mM potassium phosphate buffer (pH 7.5). Reaction was started by addition of 10 µL of $H_2O_2$ (3% v/v) and the decrease in absorbance at 240 nm was monitored for 5 min. Baseline correction was done by subtracting the absorbance taken without addition of $H_2O_2$. The assay was performed in triplicates and the absorbance values obtained were plotted against time.

The vanadate inhibited $H^+$ ATPase activity was determined for ECM and plasma membrane fraction with 20 µg of protein in 120 µl of assay buffer The assay was performed in presence and absence of 0.1 orthovanadate, freshly prepared and boiled in buffer prior to addition of 0.05% triton X-100. The assay was performed in presence of a detergent to expose all hidden sites for the cell wall bound plasma membrane, if any. The reaction was initiated by addition of ATP and was incubated at 37° C. for 30 min. Blanks lacking $MgSO_4$ were run in parallel (Larsson et al., 1994) and the released inorganic phosphate was determined (Ames, 1966). The relative activity of the enzyme was calculated by taking the difference between the absorbance at 700 nm in absence and presence of orthovanadate.

Phosphotungstic Acid Staining (PTA)

PTA at low pH can be used to stain specifically the plasma membrane in thin sections for electron microscopy (Larsson et al., 1994). Thin sections of glutarladehyde and osmium tetroxide fixed purified ECM fraction were lifted on nickel grids and destained by placing a droplet of 1% (w/v) periodate, pH 3.0 for 15 min at 20° C. and rinsed for 5 min with distilled water. The grid was then incubated in 1% PTA, pH 3.0 for 10 min at 37° C. and rinsed with 1 mM HCl. The specificity of the PTA staining to plasma membrane was checked on a section of leaf tissue.

Example 3

2-Dimensional Gel Electrophoresis and Protein Identification

The ECM proteins were precipitated with 100% acetone after boiling in dilution buffer (Hurkman and Tanaka, 1986). Protein pellets were washed twice with 80% acetone, air dried and resuspended in 2-D rehydration buffer [8 M urea, 2 M thiourea, 4% (w/v) CHAPS, 20 mM DTT, 0.5% (v/v) pharmalyte and 0.05% (w/v) bromophenol blue]. Isoelectric focusing was carried out with 300 µg protein in 350 µL 2-D rehydration buffer for 18 cm pre-cast gel strips (pH 4-7). Electrofocusing was performed using IPGphor system at 20° C. for 40,000 Vh for 18 cm gels. The focused strips were subjected to reduction with 1% (w/v) DTT in 10 mL of equilibration buffer [6 M urea, 50 mM Tris-HCl (pH 8.8), 30% (v/v) glycerol and 2% (w/v) SDS], followed by alkylation with 2.5% (w/v) iodoacetamide in the same buffer. The strips were then loaded on top of 12.5% polyacrylamide gels for SDS-PAGE. The electrophoresed proteins were stained with silver stain plus kit and images were digitized with a FluorS equipped with a 12-bit camera.

A 2D gel of ECM proteins revealed approximately 450 protein spots evenly distributed between pH 4 and 7 and molecular masses of 14 to 120 kDa. The gel images were analyzed by the PD Quest software, followed by filtering of low-quality data, girding the spots, and determination of expected molecular mass and pI of each spot. A total of 376 spots survived the filtering process, which were numbered as CaE-1 to CaE-376, [the alphabets identify the organism (*Cicer arietinum*) and the subcellular organelle (ECM) from which the proteome map has been made, whereas the numerals indicate the spot numbers].

To identify dehydration responsive ECM proteins, a comparative proteomic analysis was conducted. ECM proteins were isolated from control and dehydration treated chickpea seedlings and subjected to 2-D gel electrophoresis. The DRPs (dehydration responsive proteins) were identified by MS-MS analysis, wherein five differential spots corresponding to Ferritin were identified (FIG. 3).

The dynamics of the chickpea ECM proteome was studied under progressive dehydration conditions. Of the protein spots displaying greater than 2.5-fold upregulation or downregulation, 153 proteins were subjected to identification with LC-MS/MS. Among the dehydration-responsive components, 5 spots (spot numbers 87a, 87b, 40, 68 and 143) representing CaFer, were initially selected for further characterization. Four additional spots (55, 70, 71, and 74b) were identified as the members of the ferritin gene family that have the theoretical pI values between 5.2 and 5.6 and the peptide masses from the spectra matched that of Ferritin in the database search, indicating that all the spots represent CaFer protein. CaFer is an interesting ECM component for the following reasons: (1) ferritins participate in essential cellular processes in animal cells (Beard and Connor, 2003; Casanueva and Viteri, 2003; Ferreira et al., 2000); (2) plant ferritin gene is regulated by a complex interplay of transcriptional and posttranscriptional mechanism, involving cellular relays such as hormones, and oxidative steps (Briat et al., 1999); and (3) its localization in the ECM is suggestive of its role in plant defense against environmental stress.

Protein Identification Using MS/MS

Electrospray ion trap LC-MS/MS analysis was done using Q-Star Pulsar i (Applied Biosystems) or LCQ DECA XP Plus (Finnigan). The spectra were analyzed either by Mascot sequence matching software (www.matrixscience.com) and the Viridiplantae (green plants) database or Sequest Algorithm searching against all organism databases.

Example 4

Immunodetection and Localization of CaFer1

The presence of CaFer1 in chickpea ECM was investigated by immunoblot analysis of proteins isolated from ECM along with chloroplast and nuclear fractions using CaFer1 specific antibody. CaFer1 was found in the ECM as well as in the chloroplast fractions, but not in the nuclear fraction (FIG. 2A). The result suggests that in chickpea, CaFer1 is present both in ECM and chloroplast. As many as eight spots were identified including a cluster of five (FIG. 2B) in 2-DE. To confirm their identity, a 2-D immunoblot of the protein spots was carried out using ferritin-specific antibody. At least four spots in the designated cluster showed CaFer1 specificity (FIG. 2C). Spot 87b did not show any signal and this may be attributed to the changes in epitope caused by post translational modification of the CaFer1 isoforms.

To further confirm the presence of CaFer family members in the ECM, the subcellular localization of CaFer1 was studied by immunocytochemistry. In consistence with the immunoblot results, CaFer1 was found in ECM and chloroplasts (FIG. 2D-2F). These results confirm CaFer1 as ECM residents besides their presence in classical subcellular compartments, the chloroplast.

Example 5

Immunoblotting

Immunoblotting was done by resolving the protein on a uniform 12.5% SDS PAGE and then electrotransferring onto nitrocellulose membrane at 150 mA for 2 h. The membranes were probed with rabbit polyclonal human anti-ferritin antibody diluted to 1:5000 in Tris-buffered saline (TBS). Antibody bound proteins were detected by incubation with alkaline phosphatase conjugated anti-rabbit IgG as secondary antibody.

Example 6

Immunoelectron Microscopy

Chickpea leaflet sections were fixed in 4% paraformaldehyde and 1% glutaraldehyde in 0.1 M PBS (pH 7.2), dehydrated over grades of ethanol at 4° C., and embedded in LR-white resin (Hard). Thin sections (60-90 nm) lifted onto 400 mesh nickel grids was blocked with 3% BSA in TBS for 1 h at room temperature. Immunolabelling was done with polyclonal rabbit anti-human ferritin antibody diluted to 1:1000 in TBS. The grids were incubated with AuroProbeEM GAR G15 at a dilution of 1:50 in TBS containing 0.5% Tween 20 for 1 h at room temperature. Grids were post-fixed in 2.5% glutaraldehyde in 0.1 M PBS (pH 7.2) for 10 min and stained with 2% aqueous uranyl acetate for 20 min at room temperature and micrographed with a transmission electron microscope.

Example 7

Cloning of ECM-Localized Ferritin

Proteomic analysis of the chickpea ECM revealed three sequence tags for CaFer1. The conserved MS sequence (ES-SEEEREHAEKL; SEQ ID NO:5) was used to design the ferritin gene specific primer having oligonucleotide sequence as set for in SEQ ID NO:1.

```
Primer 1: 5'gAAgAAAgAgAgCATgCTg 3'    SEQ ID NO: 1
```

The partial clone (0.6 Kb) was obtained by 3'-RACE technique using chickpea RNA. The clone was sequenced and its identity was confirmed by database BLAST. This partial clone was used to screen a chickpea cDNA library to obtain the full-length CaFer1.

Nucleotide sequence of the partial clone of CaFer1 (SEQ ID NO: 2). The clone was sequenced and the identity was confirmed by BLAST search.
Full-Length cDNA Clone for Ferritin
A cDNA library was made with RNA isolated and pooled from dehydration stressed chickpea seedlings during 192 h of stress followed by a recovery period of 24 h. The library was screened using the $^{32}$P-labeled partial ferritin cDNA as probe (SEQ ID NO: 2). A full-length ferritin clone (1078 bp) was obtained and designated as CaFer1 (SEQ ID NO: 3). The full-length sequence of ferritin gene was analyzed in silico and a 765 by long ORF with 112 by of 5' UTR and 201 by of 3' UTR was identified for ferritin. The gene sequence was translated in six frames to get the protein sequence for ferritin. The right translation frame was identified by matching the sequence tags obtained for the protein spots in 2-D gel. The protein size was calculated to be around 28 kDa as determined by 2-D gel.

Example 7

Expression of CaFer1 in Response to Dehydration

In order to check the expression level of CaFer1 under dehydration, the difference in the transcript level was analyzed by Northern blot analyses. The level of expression of ferritin increased at 48 h but showed a marginal drop at 72 h under dehydration (FIG. 4A). A strong induction of CaFer1 transcript was observed during 96-120 h, which returned to basal level 120 h of dehydration. The transcript levels were co-related with the levels of protein expression as indicated by immunoblot analysis under dehydration at various time points. A constant induction in the protein levels was observed between 48-120 h (FIG. 4B), which corroborates with the differential display of ferritin observed in 2-DE.

Example 8

Expression of CaFer1 in Response to Other Environmental Stresses

The level of CaFer1 expression was further investigated by Northern blot analysis under high salt and ABA treatment. The CaFer1 transcripts were induced by high salt (250 and 500 mM) while no induction was observed at 100 mM salt concentration (FIG. 5A). Further, CaFer1 expression level was induced by ABA application after 4 h of stress treatment (FIG. 5B). The induced expression of CaFer1 under high salt and ABA treatment beside dehydration suggest that ferritin may participate in the ABA dependent signaling in stress responsive pathway.

Example 9

Stress Treatments

The chickpea seedlings were grown as described in Example 1. A gradual dehydration condition was applied on the 3-week-old seedlings by withdrawing water and tissues were harvested at every 24 h up to 192 h. The pots were then re-watered allowing complete recovery for 24 h and tissues were harvested. Salt stress was applied on pot grown three-week-old chickpea seedlings. The plants were supplied with half-Hoagland's medium everyday till three weeks followed stress treatment by different concentrations of NaCl (100, 250, and 500 µM) in the same medium the next day. The tissues under stress were harvested 24 h after the treatment. ABA stress was given by spraying 100 µM solution of ABA on the leaves of three-week-old chickpea seedlings and tissues were harvested every 2 h after stress treatment for 6 h. The harvested tissues were instantly frozen in liquid nitrogen and stored at –80° C.

Example 10

RNA Blot Hybridization

Total RNA was extracted from control and dehydration treated chickpea seedlings using TriPure Isolation Reagent (Roche Diagnostics, Indianapolis). Using formaldehyde as a denaturant, 30 µg of total RNA was subjected to gel electrophoresis (1.2%). Ethidium bromide staining under UV light was used to ascertain equal gel loading and efficient transfer to nylon membrane. [α-$^{32}$P]CTP labeled partial ferritin cDNA was used as the probe. The membrane was hybridized in 50% formamide (w/v) hybridization buffer at 42° C. for 18 h. Washing was as follows: 2×SSC at room temperature for 5 min, 2×SSC and 0.1% (w/v) SDS at room temperature for 5 min; 0.1×SSC and 0.5% (w/v) SDS at 42° C. for 5-10 min. The film was exposed to KODAK X-ray film and autoradiographed.

Example 11

RNA-Interference Based Ferritin Gene Silencing in *Arabidopsis*

*A. thaliana* ferritin gene family has four members, viz, AtFer1-4. The entire cDNA sequence of CaFer1 was aligned with paralogs from *Arabidopsis* using ClustalW, which recognized a 300 by homologous region. Primers, Forward 5'GGGGACAAGTTTGTACAAAAAAGCAG-GCTCAACCCACGCTTTGTATGC ATATTTCG3' (SEQ ID NO: 5) and Reverse 5'GGGGACCACTTT GTACAA-GAAAGCTGGGT CTCCCCAATGAAAGAGCCAACTCC 3' (SEQ ID NO: 6), were designed with Gateway protocol adaptors (Invitrogen, USA) in order to amplify this homologous region.

```
Primer 2:
                                        SEQ ID NO: 5
GGGGACAAGTTTGTACAAAAAAGCAGGCTCAACCCACGCTTTGTATGCAT
ATTTCG Primer 3:
                                        SEQ ID NO: 6
5'GGGGACCACTTTGTACAAGAAAGCTGGGTCTCCCCAATGAAAGAGCCA
ACTCC
```

The amplified product was cloned into pFGC5941 using Gateway vector conversion kit (Invitrogen, Carlsbad, Calif.) and maintained in DB3.1 strain of *E. coli*. The plasmid containing the RNAi cassette was isolated and transformed into *Agrobacterium* strain GV3101 by electroporation and eventually into *Arabidopsis* (Co10 background). The F1 seeds obtained were selected in MS media supplemented with BASTA (4-glufosinate ammonium; Crescent Chemicals, New Jersey, USA). This F1 population was selfed to obtain the homozygous F2 population which was used to analyze for phenotype, if any, indicative of ferritin gene function under stress. A total of 32 RNAi plants were selected and one of the putative plants was taken for further characterization.

Phenotypic Screening of atferi Plants Under Different Environmental Stresses

To assess the functional role of ferritin under different environmental stresses, the seed germination assay of atferi plants was carried out.

Example 12

Sensitivity of atferi Plants to Various Abiotic Stress

Sensitivity of atferi Plants to $H_2O_2$

The atferi seeds were allowed to germinate on MS media supplemented with 20 mM $H_2O_2$. The seeds of ferritin RNAi plants did not show any germination as compared to Co10 control seeds which showed a 100% rate of germination. The sensitivity of ferritin RNAi plants to $H_2O_2$ is corroborative with earlier findings (Deak et al., 1999) and it can be inferred that ferritin plays an important role in oxidative stress tolerance.

Sensitivity of atferi Plants to Osmotic Stress

In order to confirm the role of ferritin under osmotic stress, germination experiment was done by creating a water potential of 0.5 ψ using PEG. The atferi seeds failed to germinate under osmotically challenged conditions as compared to 90% germination for Co10 seeds. It is thus suggested that ferritin may be directly involved in dehydration tolerance mechanisms in plants. Also, the induced expression of ferritin under dehydration in chickpea indicates its possible role in osmotic stress tolerance mechanism.

Sensitivity of atferi Plants to NaCl

There are many reports on crosstalk between high salt and dehydration stress pathways (Shinozaki and Shinozaki, 1997) in plants. The osmotic stress is induced under salt stress as there is decreased availability of water due to accumulation of ions. The atferi seeds were germinated on MS media supplemented with 150 mM NaCl along with the control Co10 seeds. The seeds did not germinate on the salt supplemented media as compared to Co10 seeds which showed 100% germination under identical conditions. These results suggest that ferritin may be involved in salt stress response.

Sensitivity of atferi Plants to ABA Application

Earlier studies suggest that phytohormone ABA plays a crucial role in dehydration and salt stress response (Shinozaki and Yamaguchi-Shinozaki, 2000). To test this hypothesis, germination assay of atferi seeds was carried out in MS media containing 1 µM ABA. aba-2 are known to be sensitive to ABA and thus were used as negative control in this experiment. The atferi seeds did not germinate in the ABA supplemented medium, however, Co10 seeds germinated. The aba-2 showed defective germination as the growth of the plant was impaired after radicals emerged. The results suggest that involvement of ferritin in dehydration and salt stress responsive pathway is presumably mediated by ABA.

Example 13

Construction of Plant Expression Vector for CaFeR1

The basic plasmid pCaFer1 was constructed by PCR amplification of CaFeR1 coding region and cloning into pGEMT easy vector (Promega). In order to express CaFeR1 in plants, the full length cDNA was subcloned in a binary vector and was named as pCAF1 (FIG. 6). The plasmid construct pCAF1 was mobilized into *Agrobacterium* strain by triparental mating technique (Van Haute et al., 1983) or by standard electroporation method.

Example 14

Plant Transformation for Over-Expression of CaFer1

Any of the various methods known for introducing foreign genes into plants can be used for insertion of pCaFer1 gene into a host plant. The methodology chosen to accomplish plant transformation with the said gene varies depending on the host plant. By way of example, one well-characterized methodology that would be useful for plant transformation with pCaFer1 gene is *Agrobacterium* mediated transformation.

*Agrobacterium* mediated transformation using the pCAF1 plasmid follows the procedure well-known for this methodology. A gene cassette suitable for expression in plants is introduced into a disarmed strain of *Agrobacterium tumefaciens* as in intermediate host. The CaFer1 gene cassette is introduced into the T-DNA region of a recombinant plasmid containing a selectable marker gene such as a gene encoding for neomycin phosphotransferase II, phosphinothricin acetyl transferase, or the like. This methodology is set forth in many literature publications including Horsch et al, (1985, Science 227: 1229-1231). Various explants like leaf, cotyledons, hypocotyl, and embryo were co-cultivated with the *Agrobacterium* comprising the environmental stress responsive gene CaFer1 for 2-3 days. The explants were then transferred the selection medium containing cefotaxime. Antibiotics corresponding to the selectable marker gene were included in the plant tissue culture medium to select the transformed tissue.

Plants regenerated from the transformed cells were then analyzed for the presence and expression of the pCaFer1 gene. Immunoassays for CaFer1 protein was carried out to identify individual transformants.

Transformation of *Arabidopsis*

*Arabidopsis* (Co10) was transformed with *Agrobacterium* containing the plant expression plasmid, pCAF1 Single colony of *Agrobacterium* strain GV3101 was inoculated in 50 ml YEP medium supplemented with 50 µg/ml rifampicin and 50 μg/ml kanamycin. Culture was incubated at 28° C. with shaking at 200 rpm for 48 h, until the $OD_{600}$ reached 0.8. The floral portions of 4-6 weeks old *Arabidopsis* plants were dipped in the *Agrobacterium* culture for 10 s. The pot was wrapped in saran wrap and kept in dark for 48 h before being maintained in long day condition, 16 h photoperiod. The seeds obtained from these plants (F1) were selfed to generate F2 homozygous plants which were used for further studies.

The knockout mutants of *Arabidopsis* were generated using RNAi based plasmid for CaFer1 gene, pCAF11 by the same methodology mentioned above.

```
SEQ ID NO: 2 (458 nt)
GAAGAAGAAAGAGAGCATGCTGAGAAATTGATGGAATATCAGAACAAAAG
GGGTGGAAAAGTGAAGTTGCAATCTATAGTGAAGCCGCTTTCTGAGTTTG
ATCATGCTGATAAGGGTGATGCGCTTTACGCAATGGAACTCGCACTGTCA
TTGGAGAAGCTAACCAATGAAAAGCTCCTTAACCTGCACAATGTTGCCTC
GAAGAATGGTGACGTGCAATTGACAGACTTTGTGGAAAGTGAGTTTTTGG
GTGAACAGGTGGAAGCCATCAAAAAAATCTCAGAGTTTGTCGCTCAGCTT
AGAAGAGTTGGCAAAGGACACGGTGTCTGGCACTTTGATCAGATGTTGCT
CAACGAGGAAGCAGCTGCAGCTTGATGATTACATTTTTGTCTCCGTTTTC
AGTCATTGTATCTGTTTCTGCTAGAACTACAAGTTGACACTGAAATCGTC
AGCTGAAT

SEQ ID NO: 3 (1078 nt)
ACGGGATCGGCCATTACGGCCGGGGTCACACACATTCATCAAAACCCTTT
CTATTCCATTTTCCTCCGATTTTCTTTCTTTCCGTTTTCGTTCCGTCGAA
AATTCCCTAACCATGCTTCTCAGAGCCGCTGTAACCGCTTCTTCTTCTTC
CTCACTTCCTCTCTTCAATTCTGAAAACTCGCGTTTGGCTCCGATTCTTC
ACAGAGGAGGTAAATTGGACCGATTGGTTTTTTCCGCCACCAAAGGCTCT
AGCAATAACCGTATTCTAACCGGTGTTTTGTTTGAACCGTTTGAAGAGGT
TAAAAAGGAACTCGATCTTGTTCCCATTGTTCCTCAAGATTCCTTAGCTC
GTCGTAAGTTTCATGATGCATCTGAAGCTGCTATCAATGAACAAATCAAT
GTGGAGTATAATGTATCCTACGTTTATCATGCAATGTATGCGTACTTCGA
TAGGGATAATGTTGCCCTAAGGGGTCTTGCTAAATTTTTAAGGAATCTA
GTGAAGAGGAAAGGGAGCATGCTGAGAAATTGATGGAATATCAGAACAAA
AGGGGTGGAAAAGTGAAGTTGCAATCTATAGTGAAGCCGCTTTCTGAGTT
TGATCATGCTGATAAGGGTGATGCGCTTTACGCAATGGAACTCGCACTGT
CATTGGAGAAGCTAACCAATGAAAAGCTCCTTAACCTGCACAATGTTGCC
TCGAAGAATGGTGACGTGCAATTGACAGACTTTGTGGAAAGTGAGTTTTT
GGGTGAACAGGTGGAAGCCATCAAAAAAATCTCAGAGTTTGTCGCTCAGC
TTAGAAGAGTTGGCAAAGGACACGGTGTCTGGCACTTTGATCAGATGTTG
CTCAACGAGGAAGCAGCTGCAGCTTGATGATTACATTTTTGTCTCCGTTT
TCAGTCATTGTATCTGTTTTGCTAGAACTAGAAGTTGACACTGAATCGTA
GCTGAATAAAATTAATGTGGAATGTTTTGGGTCATTGTTAATTTTCAGTT
TATTTACCTCTTTCTCCCCAAAAAAAAAAAAAAAAAAAAAAAAAAACATG
TCGGCCGCCTCGGCCCAGTCGACTCTAG

SEQ ID NO: 4 (254 a.a.)
MLLRAAVTASSSSSLPLFNSENSRLAPILHRGGKLDRLVFSATKGSSNNR
ILTGVLFEPFEEVKKELDLVPIVPQDSLARRKFHDASEAAINEQINVEYN
VSYVYHAMYAYFDRDNVALRGLAKFFKESSEEEREHAEKLMEYQNKRGGK
VKLQSIVKPLSEFDHADKGDALYAMELALSLEKLTNEKLLNLHNVASKNG
DVQLTDFVESEFLGEQVEAIKKISEFVAQLRRVGKGHGVWHFDQMLLNEE
AAAA
```

REFERENCES

Ambe, S., Ambe, F. & Nozuki, T. (1987) Mossbauer study of iron in soybean seeds. J. Agrie. Food Chem. 35: 292-296.

Burton, J. W., Harlow, C., Theil, E. C. (1998) Evidence for reutilization of nodule iron in soybean seed development. J Plant Nutr 21: 913-27.

Ames, B. N. (1966) Method Enzymol. 8: 113-114.

Averyhart-Fullard, V., Datta, K., Marcus, A. (1988) Proc. Natl. Acad. Sci., U.S.A. 85: 1082-1085.

Beard, J. L., Connor, J. R. (2003) Annu Rev Nutr. 23: 41-58.

Briat, J. F., Lobreaux, S., Grignon, N., Vansuyt, G. (1999) Cell. Mol. Life. Sci. 56: 155-166.

Casanueva, E., Viteri, F. E. J. (2003) Nat. 133: 1700-1708.

Dreger, M. (2003) Eur. J. Biochem. 270: 589-603.

Ferreira, F., Bucchini, D., Martin, M. E., Levi, S., Arosio, P. et al. (2000) J. Biol. Chem. 275: 3021-24.

Hurkman, W. J. Tanaka, C. K. (1986) Plant Physiol. 81: 802-806.

Larsson, C., Sommarin, M., Widell, S. (1994) Method Enzymol. 228: 451-469.

Stuart, D. A., Varner, J. E. (1980) Plant Physiol. 66: 787-792.

Kwok, J. C., Richardson, D. R. (2004) Mol. Pharmacol. 65: 181-195.

Harrison, P. M., Arosio, P. (1996) The ferritins: molecular properties, iron storage function and cellular regulation. Biochim. Biophys. Acta 1275: 161-203.

Deak, M., Horvath, G. V., Davletova, S., Torok, K., Sass, L., Vass, I., Bama, B., Kiraly, Z., Dudits, D. (1999) Plants ectopically expressing the iron-binding protein, ferritin, are tolerant to oxidative damage and pathogens. Nat. Biotechnol. 17: 192-196.

Shinozaki, K., Yamaguchi-Shinozaki, K. (1997) Gene expression and signal transduction in water-stress responses. Plant Physiol. 115: 327-334.

Shinozaki, K, Yamaguchi-Shinozaki, K (2000) Molecular responses to dehydration and low temperature: differences and cross-talk between two stress signaling pathways. Curr. Opin. Plant Biol. 3: 217-223.

Haute, E. V., Joos, H., Maes, M., Warren, G., Montagu, M. V and Schell, J. (1983) Intergeneric transfer and exchange recombination of restriction fragments cloned in pBR322: a novel strategy for the reversed genetics of the Ti plasmids of *Agrobacterium tumefaciens*. EMBO J. 2: 411-417.

Horsch, R. B., Fry, J. E., Hoffman, N. L., Eichholtz, D., Rogers, S. G. and Fraley, R. T. (1985) A simple and general method for transferring genes into plants. Science, 227: 1229-1231.

We claim:
1. An isolated nucleic acid encoding a polypeptide comprising the amino acid of SEQ ID NO: 4.
2. A recombinant vector comprising the nucleic acid of claim 1.
3. A recombinant host cell comprising a construct comprising the nucleic acid of claim 1.
4. The recombinant host cell of claim 3, wherein said recombinant host cell comprises the nucleic acid of SEQ ID NO: 3.

5. The recombinant host cell of claim 3, wherein the recombinant host cell is selected from the group consisting of *E. coli, Agrobacterium*, and yeast.

6. The isolated nucleic acid of claim 1, wherein said nucleic acid comprises SEQ ID NO: 3.

7. A method for producing a transformed plant cell, plant, or plant part expressing a ferritin, said method comprising transforming a plant cell, plant or, plant part with a nucleic acid construct encoding a ferritin comprising the amino acid sequence of SEQ ID NO: 4, wherein said transformed plant cell, plant, or plant part is tolerant to an environmental stress.

8. The method of claim 7, wherein the plant is a monocot or dicot.

9. The method of claim 8, wherein the monocot is selected from the group consisting of rice, wheat, barley, rye, corn, sorghum, and sugarcane.

10. The method of claim 8, wherein the dicot is selected from the group consisting of potato, carrot, sweet potato, cassava, bean, chickpea, pigeonpea, pea, cabbage, cauliflower, eggplant, soybean, and tomato.

11. A dehydration stress tolerant transgenic plant cell, plant, or plant part which expresses a nucleic acid encoding a ferritin comprising the amino acid of SEQ ID NO: 4.

12. The dehydration stress tolerant transgenic plant cell, plant, or plant part of claim 11, wherein said plant cell, plant, or plant part that contains a construct that expresses the nucleic acid comprising SEQ ID NO: 3.

13. A seed of the transgenic plant of claims 11 or 12, wherein the seed contains the nucleic acid construct encoding a ferritin comprising the amino acid of SEQ ID NO: 4.

14. A progeny plant produced from the transgenic plant cell, plant, or plant part of claims 11 or 12, wherein said progeny plant comprises a nucleic acid construct encoding a ferritin comprising SEQ ID NO: 4.

15. An environmental stress tolerant transgenic plant cell, plant, or plant part which expresses a nucleic acid encoding a ferritin comprising the amino acid of SEQ ID NO: 4.

16. The environmental stress tolerant transgenic plant cell, plant, or plant part of claim 15, wherein said plant cell, plant, or plant part that contains a construct that expresses the nucleic acid comprising SEQ ID NO: 3.

17. A seed of the transgenic plant of claims 15 or 16, wherein the seed contains nucleic acid construct encoding a ferritin comprising the amino acid of SEQ ID NO: 4.

18. A progeny plant produced from the transgenic plant cells, plant, or plant part of claims 15 or 16, wherein said progeny plant comprises a nucleic acid construct encoding a ferritin comprising SEQ ID NO: 4.

* * * * *